United States Patent [19]

Friese et al.

[11] Patent Number: 5,698,267

[45] Date of Patent: Dec. 16, 1997

[54] METHOD FOR FABRICATING HIGH-ACTIVITY ELECTRODES FOR EXHAUST GAS SENSORS

[75] Inventors: Karl-Hermann Friese, Leonberg; Hans-Martin Wiedenmann, Stuttgart; Frank Stanglmeier, Möglingen, all of Germany

[73] Assignee: Robert Bosch GmbH, Stuttgart, Germany

[21] Appl. No.: 728,797

[22] Filed: Oct. 10, 1996

Related U.S. Application Data

[63] Continuation of Ser. No. 446,613, filed as PCT/DE93/01136, Nov. 27, 1993 published as WO94/12870, Jun. 9, 1994, abandoned.

[30] Foreign Application Priority Data

Dec. 1, 1992 [DE] Germany .......................... 42 40 267

[51] Int. Cl.$^6$ .......................... B05D 1/18; G01N 27/406
[52] U.S. Cl. .......................... 427/430.1; 204/421; 204/424; 264/DIG. 36; 264/104; 264/603; 264/614; 264/618; 427/435; 427/436; 427/443.2
[58] Field of Search .......................... 204/421–429; 427/430.1, 435, 436, 443.2; 264/603, 614, 618, 104, DIG. 36

[56] References Cited

U.S. PATENT DOCUMENTS

| | | | |
|---|---|---|---|
| 3,843,400 | 10/1974 | Radford et al. | 204/421 |
| 3,978,006 | 8/1976 | Topp et al. | 204/429 |
| 3,989,614 | 11/1976 | Tien | 204/427 |
| 4,199,425 | 4/1980 | Sinkevitch | 204/429 |
| 4,283,441 | 8/1981 | Haecker et al. | 204/429 |
| 4,372,824 | 2/1983 | Toda et al. | 205/122 |
| 4,530,751 | 7/1985 | Ishiguro | 204/424 |
| 4,655,892 | 4/1987 | Satta et al. | 204/421 |
| 4,789,561 | 12/1988 | Schaefer et al. | 204/421 |
| 4,940,528 | 7/1990 | Oki et al. | 204/426 |
| 5,141,825 | 8/1992 | Jensen | 429/31 |
| 5,380,424 | 1/1995 | Friese et al. | 204/429 |
| 5,443,711 | 8/1995 | Kojima et al. | 204/429 |

FOREIGN PATENT DOCUMENTS 2619746  11/1977  Germany .

*Primary Examiner*—T. Tung
*Attorney, Agent, or Firm*—Spencer & Frank

[57] ABSTRACT

A method for fabricating a high-activity cermet electrode which is applied on an exhaust gas sensor including an oxygen ion conducting solid electrolyte, which is composed of a cermet material composed of at least one catalytically active material and at least one oxygen ion conducting ceramic material, which is bonded to the solid electrolyte of the exhaust sensor by co-sintering the cermet electrode and the solid electrolyte at a temperature ranging from 1300° to 1600° C. to provide a porous cermet electrode, and which contains at least one further catalytically active material which is embedded in the pores of the porous cermet electrode after co-sintering, the method including bonding together an unsintered solid electrolyte which conducts oxygen ions and a cermet electrode by co-sintering at from 1300° to 1600° C. to provide a porous cermet electrode; and subsequently introducing at least one further catalytically active material into pores of the porous cermet electrode.

8 Claims, No Drawings

METHOD FOR FABRICATING HIGH-ACTIVITY ELECTRODES FOR EXHAUST GAS SENSORS

This application is a Continuation of application Ser. No. 08/446,613, filed as PCT/DE93/01136, Nov. 27, 1993 published as WO94/12870, Jun. 9, 1994, now abandoned.

BACKGROUND OF THE INVENTION

It is known, e.g., from DE-A3-28 52 638, that the oxygen content of gas mixtures, for example, of exhaust gases from internal combustion engines, can be determined according to the principle of an oxygen concentration chain employing sensors which are based on the oxygen ion conductivity of certain stabilized oxides, preferably of fully or partially stabilized zirconium(IV) oxide. Suitable electrodes are e.g. the so-called cermet electrodes which are known, inter alia, from DE-A1-26 19 746. They generally comprise platinum and stabilized zirconium oxide and are eminently suitable for use in gas sensors. The platinum particles touching one another cause the gas equilibrium to be established by catalyzing the reaction of the oxygen with the oxidizable fractions of the gas mixture, and at the same time they act as electron conductors, i.e. they conduct the current which flows as a result of the ion migration in the zirconium(IV) oxide as a solid electrolyte. The stabilized zirconium(IV) oxide on the other hand establishes an ion-conducting connection between the platinum particles of the cermet electrode and the solid electrolyte.

Since the exhaust gas sensors are subject to thermal, mechanical and under certain conditions also corrosive stresses, the cermet electrodes must be bonded as firmly as possible to the solid electrolyte. This is best achieved by cosintering. This involves starting from the unsintered, finely particulate oxide mixture, suitably shaped for subsequent use, which after sintering produces the solid electrolyte, and applying the matrix of the subsequent cermet electrode to the molding thus produced, for example by applying a paste of a finely particulate platinum/zirconium (IV) oxide mixture to the molding. After drying, the solid electrolyte and the cermet electrode are firmly sintered together, generally at from 1300° to 1600° C.

The cermet electrodes are then bonded virtually inseparably to the solid electrolyte. The electrical properties of the electrodes are not fully satisfactory, however. Cermet electrodes which were exposed to the high sintering temperatures are distinctly less sensitive and less stable under load than the unsintered ones. They show a higher tendency toward polarization, i.e. a counter-e.m.f. builds up which may attenuate the voltage signal of the probe to such an extent that it can no longer be evaluated without complicated amplification.

SUMMARY OF THE INVENTION

The highly sensitive electrodes, fabricated in accordance with the methods and used in accordance with the present invention combine a high thermal, mechanical and corrosion stability, which results from the sinter bonding of electrode and solid electrolyte, with a sensitivity or stability under load such as had hitherto been a characteristic only of unsintered cermet electrodes. Sensors comprising the electrodes according to the invention have a long service life and do not require complicated amplification of the voltage signals. Moreover, these sensors are distinguished by an unusually narrow scatter of the measurement results of different specimens of the same type, in particular at low application temperatures, e.g. below 300° C.

DESCRIPTION OF THE PREFERRED EMBODIMENTS

The electrodes primarily comprise the conventional cermet electrodes and the conventional solid electrolytes. For the sake of a firm sinter bonding, it is expedient to select the same metal oxides for the cermet electrode and for the solid electrolyte. Advantageously, the material employed for the solid electrolyte is partially stabilized zirconium(IV) oxide and that for the matrix of the cermet electrode is fully stabilized zirconium(IV) oxide, as described in DE-A3-28 52 638.

The quantitative ratios of the metallic and the ceramic constituents should be proportioned in such a way that, on the one hand, the platinum particles touch one another and enable the conduction of electrons and, on the other hand, enough zirconium(IV) oxide is present for the conduction of oxygen ions. In general, the platinum proportion is between 50 and 80% by volume. During the sintering process a fine pore structure is produced which facilitates the subsequent application of catalytically active material.

The solid electrolyte as a rule comprises zirconium(IV) oxide which is stabilized with an oxide of a trivalent metal of the second subgroup of the Periodic Table of the Elements, expediently partially stabilized, for example With scandium oxide, but preferably with yttrium oxide or an oxide of an element of the higher rare earths. The term higher rare earths is to be understood as meaning those having an atomic number >64. Examples to be mentioned are erbium(III) oxide, dysprosium(III) oxide and ytterbium (III) oxide. The optimum amounts for partial stabilization can readily be determined by preliminary experiments. In the case of the system zirconium(IV) oxide/ytterbium(III) oxide they are between 4 and 7 mol %. Instead of or in addition to zirconium(IV) oxide it is also possible to employ the other metal oxides known as ion conductors, eg. hafnium (IV) oxide or cerium(IV) oxide.

In order to fabricate the electrodes according to the invention, the finely particulate material which later forms the solid electrolyte is molded in a conventional manner into the desired shape, for example a tube closed at one end, as known from DE-A2-22 65 309. Then the mixture which later becomes the cermet electrode is applied as a paste or suspension at the point or points at which the cermet electrode is desired. In the case of sensors for exhaust gases of internal combustion engines this is the outside and the inside of the abovementioned tube closed at one end. Then the blank is dried and sintered at temperatures of from 1300° to 1600° C., especially of from 1350° to 1500° C., generally under atmospheric pressure. The duration of the sintering operation depends on the temperature and the materials chosen or the combination of materials and generally amounts to a holding time between 1 and 5 hours at the maximum temperature, i.e., excluding the time for heating and cooling.

It is an important feature of the invention that the cermet electrode has catalytically active material applied thereto after the sintering operation. This is what gives the electrodes their surprisingly high stability under load. The stability under load of cermet electrodes can also be increased mechanically, e.g., by roughening by means of abrasive or chemically, e.g., by an acid treatment. A more elegant and efficient method, however, is that of the invention, the porous, sintered cermet electrode having a catalytically active material applied to it. This is done advantageously by the electrode being impregnated with a solution of at least one inorganic or organic compound of a catalytically active metal such as platinum or rhodium, and the solvent being evaporated. This causes the compound to be deposited on the outer surface of the electrode but also and in particular on its inner surface, i.e., in the interior of the pores. Expediently the electrode is then tempered for some time, e.g., at from 300° to 900° C., during which operation the noble metal compound may decompose, at least partially. It is advantageous for the electrode together with the compound of the catalytically active metal then to be heated in a hydrogen stream, for example, at from 500° to 600° C., which causes metallic platinum or rhodium or a platinum-rhodium alloy to be produced. The catalyst, however, is activated even without previous reduction when first used under operating conditions, appropriate temperatures prevailing in the process. As a result, the cermet electrodes achieve the desired high sensitivity and stability under load.

The electrodes according to the invention may be coated with the usual protective layers, as has been described in DE-A2-22 65 309, DE-A3-41 00 106 or the German Patent Application P 40 33 388.4.

EXAMPLES

Test methods

1. Assessment of the a.c. internal resistance

The a.c. internal resistance at 500° C. is a measure for the quality of the bond between electrode and electrolyte. The a.c. internal resistance of the electrode according to Comparative Example 1 was taken as 100%. A lower a.c. internal resistance indicates a more intimate contact or a firmer bond between electrode and electrolyte.

2. Assessment of the polarization

A measure for the polarization is provided by the d.c. internal resistance impressed as a result of a flow of current through the electrolyte or established by loading the signal. The d.c. internal resistance of the electrode according to Comparative Example 1 was again taken as 100%. A lower d.c. internal resistance means a higher stability under load of the signal.

3. Assessment of the low-temperature behavior

The low-temperature behavior of gas sensors in the exhaust gas of an internal combustion engine was assessed. The sensors were fitted into the exhaust gas line, and the signal deviation of the sensor as a result of the oscillation of the air/fuel ratio at 300° C. was recorded. The signal deviation of the sensor comprising the electrode according to Comparative Example 1 was taken as 100%. A higher value, i.e., a larger signal deviation means an improved signal behavior at low temperatures.

The results of the tests are summarized in the table.

Example 1

(comparative example according to the prior art)

The solid electrolyte consists of zirconium(IV) oxide stabilized with yttrium(III) oxide (4 mol % of yttrium(III) oxide, 96 mol % of zirconium(IV) oxide). The cermet electrode was applied according to the method of DE-A3-28 52 638 as a paste containing 60% by volume of platinum and 40% by volume of fully stabilized zirconium(IV) oxide. The finished sensor element is obtained by cosintering at 1500° C. (5 hours).

Example 2

The sintered sensor element of Example 1 was impregnated with an aqueous solution of a catalytically active material. To this end, a solution of hexachloroplatinic(IV) acid and of rhodium(III) chloride in a weight ratio of Pt:Rh of 5:2 was used. The concentrations of the noble metals in the solutions were 1% by weight of platinum and 0.4% by weight of rhodium. The sensor element was exposed to the solution for 5 minutes at a pressure of 100 mbar, the pressure then being raised to 1 bar.

The impregnated sensor element was dried in air at 100° C. for 0.5 hours, then tempered in air at 350° C. for a further 0.5 hours, after which the precipitated noble metal compounds were reduced in a stream of hydrogen (550° C., 1 hour).

Example 3

The sintered sensor element of Example 1 was impregnated with solutions of organic platinum compounds. To this end, a solution of the platinum(II) salt of 2-ethylhexanoic acid or naphthenic acid or platinum(II) acetylacetonate in benzyl alcohol with a platinum content of 1.5% by weight in each case was used. The sensor element was impregnated and dried as in Example 2. Then it was tempered in air for 0.5 hours at 850° C. and heated at 550° C. for one hour in a stream of hydrogen.

The measurement results were virtually identical for all 3 platinum compounds mentioned.

TABLE

| | Example 1 (comparative) % | Example 2 % | Example 3 % |
|---|---|---|---|
| Test 1 a.c. internal resistance | 100 | 92 | 89 |
| Test 2 d.c. internal resistance | 100 | 85 | 86 |
| Test 3 Low-temperature behavior in the exhaust gas | 100 | 210 | 195 |

What is claimed:

1. A method for fabricating a high-activity cermet electrode which is applied on an exhaust gas sensor including an oxygen ion conducting solid electrolyte, which is comprised of a cermet material comprising at least one catalytically active material and at least one oxygen ion conducting ceramic material, which is bonded to the solid electrolyte of the exhaust sensor by co-sintering the cermet electrode and the solid electrolyte at a temperature ranging from 1300° to 1600° C. to provide a porous cermet electrode, and which contains at least one further catalytically active material which is embedded in the pores of the porous cermet electrode after co-sintering, the method comprising:

a. bonding together an unsintered solid electrolyte which conducts oxygen ions and a cermet electrode by co-sintering at from 1300° to 1600° C. to provide a porous cermet electrode;

b. subsequently introducing at least one further catalytically active material into pores of the porous cermet electrode by impregnation thereof with a solution containing a solvent and at least one compound selected from the group consisting of inorganic compounds of platinum group metals and organic compounds of platinum group metals; and c. tempering the cermet electrode at a temperature ranging from 300° to 900° C. after evaporating the solvent to thereby decompose the at least one compound and provide a metallic residue.

2. The method as claimed in claim 1, wherein the at least one oxygen ion conducting ceramic material of the cermet material is comprised of fully stabilized zirconium(IV) oxide and the at least one catalytically active material of the cermet material is comprised of platinum, and wherein the solid electrolyte is comprised of partially stabilized zirconium(IV) oxide.

3. The method as claimed in claim 2, wherein the at least one catalytically active material of the cermet material is comprised of from 50 to 80% by volume of platinum.

4. The method as claimed in claim 3, wherein the cermet material is comprised of 40% by volume of fully stabilized zirconium(IV) oxide and 60% by volume of platinum.

5. The method as claimed in claim 1, wherein the at least one further catalytically active material is a material selected from the group consisting of platinum and rhodium, and is introduced into the pores of the porous cermet electrode by impregnating the porous cermet electrode with a solution containing a solvent and at least one compound selected from the group consisting of inorganic platinum compounds, organic platinum compounds, inorganic rhodium compounds, and organic rhodium compounds, and evaporating the solvent.

6. The method as claimed in claim 5, wherein the at least one compound selected from the group consisting of inorganic platinum compounds, organic platinum compounds, inorganic rhodium compounds, and organic rhodium compounds is decomposed during tempering to provide a residue comprised of at least one of platinum and rhodium.

7. The method as claimed in claim 1, further comprising, prior to first use of the cermet electrode, heating the cermet electrode under a hydrogen atmosphere.

8. The method according to claim 1, wherein the at least one catalytically active material comprises at least one platinum group metal.

* * * * *